US012708292B1

(12) United States Patent
Fox Cotton et al.

(10) Patent No.: US 12,708,292 B1
(45) Date of Patent: Aug. 18, 2026

(54) STATE ASSESSMENT SYSTEM AND METHODS OF USE

(71) Applicant: Aptima, Inc., Woburn, MA (US)

(72) Inventors: Olivia Fox Cotton, Centerville, OH (US); Lisa Lucia, West Roxbury, MA (US); Jordan Coker, Auburn, AL (US)

(73) Assignee: Aptima, Inc., Woburn, MA (US)

( * ) Notice: Subject to any disclaimer, the term of this patent is extended or adjusted under 35 U.S.C. 154(b) by 726 days.

(21) Appl. No.: 18/067,554

(22) Filed: Dec. 16, 2022

Related U.S. Application Data

(60) Provisional application No. 63/290,573, filed on Dec. 16, 2021.

(51) Int. Cl.
*A61B 5/1455* (2006.01)
*A61B 5/145* (2006.01)

(52) U.S. Cl.
CPC ........ *A61B 5/14546* (2013.01); *A61B 5/1455* (2013.01); *A61B 2503/20* (2013.01)

(58) Field of Classification Search
None
See application file for complete search history.

(56) References Cited

U.S. PATENT DOCUMENTS 9,848,812 B1 12/2017 Harrivel et al.
2018/0042484 A1* 2/2018 Bracken ................ G01J 3/0291

OTHER PUBLICATIONS

Al-Shargie et al., Mental Stress Assessment Using Simultaneous Measurement of EEG and fNIRS. Biomedical Optics Express, Oct. 2016, vol. 7(10), pp. 3882-3898.
Al-Shargie, Stress Detection and Reduction Based on Simultaneous Measurement of EEG and fNIRS Signals. Frontiers in Human Neuroscience, Jan. 2019, vol. 13, 2 page Abstract.
Baker et al., Modified Beer-Lambert Law for Blood Flow. Biomedical Optics Express, Nov. 2014, vol. 5(11), pp. 4053-4075.
Brennan et al., Coordinating Cognition: The Costs and Benefits of Shared Gaze During Collaborative Search. Cognition, Mar. 2008, vol. 106(3), pp. 1465-1477.
Carter et al., Target predictability, Sustained Attention, and Response Inhibition. Brain and Cognition, Jun. 2013, vol. 82(1), pp. 35-42.

(Continued)

*Primary Examiner* — Marjan Fardanesh
(74) *Attorney, Agent, or Firm* — John J. Brooks, III

(57) ABSTRACT

A state assessment system is provided to determine a state of a subject with an analytics subsystem based on data from a physiological sensor. In some embodiments, the physiological sensor is a fNIRS sensor and the analytics subsystem is configured to determine a hemoglobin measure from the physiological data, determine a neural activation measure from the hemoglobin measure and determine the state of the subject based on a physiology/state model and the neural activation measure. In some embodiments, the physiology/state model is trained by monitoring the subject with the fNIRS sensor and performing a Continuous Performance Test (CPT) to determine attention data and performing an n-back task to determine workload data. In some embodiment, the state of the subject is an objective measure of one of a vigilance measure, a response inhibition measure, a resilience measure and a workload measure.

14 Claims, 10 Drawing Sheets

(56) References Cited

OTHER PUBLICATIONS

Causse et al., Influences of Age, Mental Workload, and Flight Experience on Cognitive Performance and Prefrontal Activity in Private Pilots: a fNIRS Study. Scientific Reports, May 2019, vol. 9(1), pp. 1-12.
Cummings et al., Task Versus Vehicle-Based Control Paradigms in Multiple Unmanned Vehicle Supervision by a Single Operator. IEEEE Transactions on Human-Machine Systems, Jun. 2014, vol. 44(3), pp. 353-361.
DeCostanza et al., Team Measurement: Unobtrusive Strategies for Intelligent Tutoring Systems. in Building Intelligent Tutoring Systems for Teams, vol. 19, Sep. 2018, pp. 101-130.
DeHais et al., Monitoring Pilot's Cognitive Fatigue with Engagement Features in Simulated and Actual Flight Conditions Using a Hybrid fNIRS-EEG Passive BCI. IEEE Conference on Systems, Man, and Cybernetics Society (SMC 2018), Oct. 2018, Miyazaki, Japan, 7 pages.
Dieleman et al., Short-term Mechanisms Influencing Volumetric Brain Dynamics. NeuroImage, 2017, vol. 16, pp. 507-513.
Durkee et al., System Decision Framework for Augmenting Human Performance Using Real-Time Workload Classifiers. 2015 IEEE International Multi-Disciplinary Conference on Cognitive Methods in Situation Awareness and Decision Support (CogSIMA), Orlando, Florida, Mar. 9-12, 2015, pp. 8-13.
Durkee et al., Real-Time Workload Assessment as a Foundation for Human Performance Augmentation. in Foundations of Augmented Cognition. AC/HCII 2013, LNAI 8027, 2013, pp. 279-288.
Eskicioglu et al., Brain asymmetry in directing attention during dichotic listening test: An fNIRS study. Laterality: Asymmetries of Body, Brain and Cognition, Jul. 2019, vol. 24(4), pp. 377-392, DOI: 10.1080/1357650X.2018.1527847, epub Sep. 27, 2018, 17 pages.
Fischer et al, Linguistic Correlates of Team Performance: Toward a Tool for Monitoring Team Functioning During Space Missions. Aviation, Space, and Environmental Medicine, May 2007, vol. 73(5), Section II, pp. B86-B95.
Frederick-Recascino et al., Monitoring Automated Displays: Effects of and Solutions for Boredom. Computer Science, Oct. 2001, 20th Digital Avionics Systems Conference (20th DASC), vol. 1, Oct. 14-18, 2001, Daytona Beach, FL, USA. pp. 5D3/1-5D3/5.
Fusaroli et al., A Heart for Interaction: Shared Physiological Dynamics and Behavioral Coordination in a Collective, Creative Construction Task. Journal of Experimental Psychology: Human Perception and Performance, 2016, vol. 42, pp. 1297-1310. arXiv: 1504.05750.
Gabbard et al., Utilizing functional near-infrared spectroscopy for prediction of cognitive workload in noisy work environments. Neurophotonics, Oct.-Dec. 2017, vol. 4(4), 041406, 10 pages.
Geeseman et al., Functional Near-Infrared Spectroscopy (fNIRS) in an Aerospace Environment: Challenges and Considerations. Aerospace Medicine and Human Performance, Oct. 2020, vol. 91(10), pp. 833-835.
Gidlof et al., Using Eye Tracking to Trace a Cognitive Process: Gaze Behaviour During Decision Making in a Natural Environment. Journal of Eye Movement Research, 2013, vol. 6(1), pp. 1-14.
Hasson et al., Intersubject Synchronization of Cortical Activity During Natural Vision. Science, Mar. 2004, vol. 303 (5664), pp. 1634-1640.
Heilbronner et al., Caffeine Differentially Alters Cortical Hemodynamic Activity During Working Memory: A Near Infrared Spectroscopy Study. BMC Research Notes, 2015, vol. 8:520, 7 pages. DOI 10.1186/s13104-015-1491-3.
Khan et al., Drowsiness Detection During a Driving Task Using fNIRS. Chapter 13 in Neuroergonomics, 2019, pp. 79-85.
McKendrick et al., Mobile Neuroergonomics: Action, Interfaces, Cognitive Load, and Selective Attention. Chapter 18 In Neuroergonomics: The Brain at Work and in Everyday Life. 2019, pp. 111-116.
Nihashi et al., Monitoring of Fatigue in Radiologists During Prolonged Image Interpretation Using fNIRS. Japanese Journal of Radiology, 2019, vol. 37(6), pp. 437-448.
Pappada et al., Establishing an Instrumented Environment for Simulation-based Training of Healthcare Providers: An Initial Proof of Concept. International Journal of Academic Medicine, Jun. 2016, pp. 32-40.
Pappada et al., Developing Neurocognitive Workload Management Technologies for Multitasking, Power Point Presentation on US Navy Panel: Human Factors Challenges in UAS—Cognitive Workload, Situational Awareness, Decision-Making, and Trust in Automation, 85th Annual Scientific Meeting of the Aerospace Medical Association (AsMA), San Diego, CA. May 15, 2014. 18 pages.
Parasuraman et al., Putting the Brain to Work: Neuroergonomics Past, Present, and Future. Human Factors, Jun. 2008, vol. 50(3), pp. 468-474.
Richardson et al., Looking to Understand: The Coupling Between Speakers' and Listeners' Eye Movements and its Relationship to Discourse Comprehension. Cognitive Science, 2005, vol. 29, pp. 39-54.
Sestito et al., Investigating Neural Sensorimotor Mechanisms Underlying Flight Expertise in Pilots: Preliminary Data from an EEG Study. Frontiers in Human Neuroscience, Dec. 2018, vol. 12, Art. 489, 13 pages.
Stewart et al. Eye Movements in Strategic Choice. Journal of Behavioral Decision Making, 2016, vol. 29, pp. 137-156.
Strang et al., Physio-Behavioral Coupling in a Cooperative Team Task: Contributors and Relations. Journal of Experimental Psychology: Human Perception and Performance, Jun. 2013, vol. 40(1), pp. 145-158, 16 pages.
Tekleab et al., A Longitudinal Study of Team Conflict, Conflict Management, Cohesion, and Team Effectiveness. Group & Organization Management, Apr. 2009, vol. 34(2), pp. 170-205.
Thayer, On the Importance of Inhibition: Central and Peripheral Manifestations of Nonlinear Inhibitory Processes in Neural Systems. Dose-Response. Jan.-Mar. 2006, vol. 4, pp. 2-21.
United States Air Force Aircraft Accident Investigation Board Report, F-16CM, T/N 94-0043, 77th Fighter Squadron, 20th Fighter Wing, Shaw Air Force Base, South Carolina. Jun. 30, 2020, Report issued Oct. 18, 2020, 49 pages.
Williams et al., Resting Cardiac Vagal Tone Predicts Intra-Individual Reaction Time Variability during an Attention Task in a Sample of Young and Healthy Adults. Psychophysiology, Oct. 2016, vol. 53(12), pp. 1843-1851, DOI: 10.1111/psyp.12739. 9 pages.

* cited by examiner

STATE ASSESSMENT SYSTEM AND METHODS OF USE

STATEMENT REGARDING FEDERALLY SPONSORED RESEARCH OR DEVELOPMENT

This invention was made with Government support under USAMRAA W81XWH20P0022 awarded by U.S. Army Medical Research Acquisition Activity. The Government has certain rights in the invention.

CROSS-REFERENCE TO RELATED APPLICATIONS

This application claims the benefit of U.S. App. No. 63,290,573, filed on Dec. 16, 2021, entitled "NEAR-INFRARED ASSESSMENT SYSTEM," the entire contents of which is incorporated herein by reference.

REFERENCE TO SEQUENCE LISTING, A TABLE, OR A COMPUTER PROGRAM LISTING COMPACT DISC APPENDIX

Not Applicable.

BACKGROUND

1. Field of the Invention

2. Description of the Prior Art

The ability to assess preparedness and fitness for duty is a challenging but important objective for military and commercial applications. The state of Warfighters (whether they are fatigued, distracted, and/or stressed) and the state of the team (whether team members are working together effectively and cohesively) greatly impact the likelihood of mission success. Compelling examples of the need for objective and quantified state assessments can be readily found in reviewing military Accident Investigation Board (AIB) reports. Recently, there was a fatality during an F-16 nighttime mission qualification training flight that required the pilot to execute his first-ever aerial refueling. This tragedy can, in part, be characterized as a failure in Operational Risk Management (ORM), as the pilot was placed in a situation for which he was not prepared. Current techniques for estimating the mission preparedness of Warfighters fall short, largely relying on subjective ratings (e.g., a commander's observational assessment of their subordinate) or self-reports (e.g., individual Warfighter's claim that they are fit for duty). This process renders it difficult—or even impossible—to assess the quality and accuracy of such judgements prior to mission start. An inaccurate estimation of Warfighters' preparedness could place them in a situation that they are not, at present, equipped to handle and could result in unnecessary risk to the health of the Warfighters and to the success of the mission, as exemplified by aircraft accidents.

BRIEF SUMMARY OF THE INVENTION

The following summary is included only to introduce some concepts discussed in the Detailed Description below. This summary is not comprehensive and is not intended to delineate the scope of protectable subject matter, which is set forth by the claims presented at the end.

In one embodiment, an assessment system is provided comprising a sensor. In some embodiments, the sensor comprises a near-infrared sensor. In some embodiments, the assessment system further comprises an analytics suite and a decision support platform.

In one example embodiment, a state assessment system configured to determine a state of a subject is provided comprising a physiological sensor configured to communicate a physiological data of a subject and an analytics subsystem configured to determine a state of the subject from the physiological data. In some embodiments, the physiological sensor comprises a fNIRS sensor comprising one or more LED and one or more photodetector. In some embodiments, the analytics subsystem comprises a hemoglobin estimation module configured to determine a hemoglobin measure from the physiological data of the subject, a neurocognitive measure module configured to determine a neural activation measure from the hemoglobin measure, a physiology/state model configured to define a relationship between a neurocognitive measure and a cognitive state, and a state measure module configured to determine the state of the subject based on the physiology/state model and the neural activation measure.

In one example embodiment, a method of training a physiology/state model for use to determine a state of a subject based on a physiological data of the subject is provided, the method comprising defining a state of the subject as an attention measure and a workload measure, defining the physiological data as a neural activation data of the subject, placing a sensor on the subject to measure the neural activation of the subject, defining an objective relationship of the attention measure to the neural activation of the subject over a time period by performing a Continuous Performance Test (CPT) on the subject and measuring the neural activation of the subject over the time period, and defining an objective relationship of the workload measure to the neural activation of the subject over a second time period by performing an n-back task on the subject and measuring the neural activation of the subject over the second time period. In some embodiments, the objective relationship of the attention measure to the neural activation of the subject and the objective relationship of the workload measure to the neural activation of the subject are defined by a machine learning algorithm.

In some embodiments, the state of the subject comprises an objective measure of an attention measure and a workload measure.

In some embodiments, the state of the subject comprises an objective measure of a vigilance measure, a response inhibition measure, a resilience measure or a workload measure.

In some embodiments, the attention measure and the workload measure are used to define a preparedness measure.

Other objects, features, and advantages of the techniques disclosed in this specification will become more apparent from the following detailed description of embodiments in conjunction with the accompanying drawings.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1:
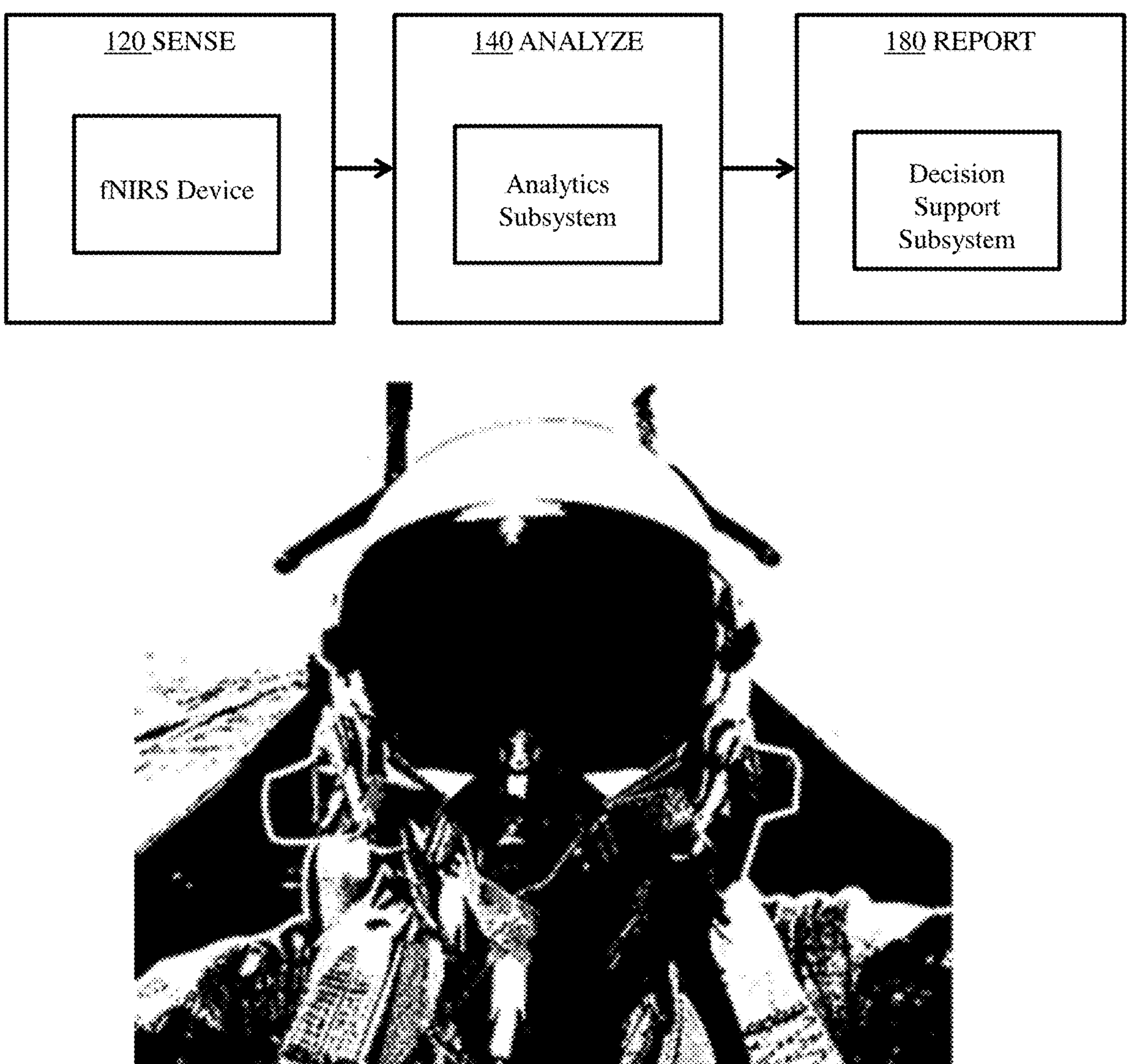
FIG. 1 illustrates a functional overview of one example embodiment of the state assessment system.

COPYRIGHT NOTICE: A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. The following notice applies to any software and data as described below and in the drawings hereto: Copyright © 2021-2022 Aptima, Inc., All Rights Reserved.

State assessment systems and methods of use will now be described in detail with reference to the accompanying drawings. Notwithstanding the specific example embodiments set forth below, all such variations and modifications that would be envisioned by one of ordinary skill in the art are intended to fall within the scope of this disclosure.

As used herein, the term “module” refers to hardware and/or software implementing entities and does not include a human being. The operations performed by the “module” are operations performed by the respective hardware and/or software implementations, e.g. operations that transform data representative of real things from one state to another state, and these operations do not include mental operations performed by a human being.

The terms “sensor data”, as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor.

The Technical Problem

Emerging technologies for physiological sensing offer complementary solutions to improve current assessment techniques and support quantified indices of team states and processes, an approach that is well. Among the many physiological measures researchers have explored, neural activity is a particularly compelling data source for quantifying human cognition and behavior. Neural monitoring across many contexts offers a profound opportunity to understand and influence individual and team Warfighter preparedness. Despite years of research showing that neural data are an ideal tool for providing accurate state measurements, a portable and ruggedized solution for in-the-field neural state monitoring does not exist.

The developing technology neural and physiological sensors can provide additional data to better assess the state on an individual or team. In particular, functional near-infrared spectroscopy (fNIRS) is better suited for operational neural state monitoring than other existing neural measurement technologies, such as functional magnetic resonance imaging (fMRI) and electroencephalography (EEG), and offers great promise for military applications. fNIRS is a non-invasive optical imaging technique that uses near-infrared light to characterize optical properties of tissue. fNIRS is a hemodynamic neuroimaging brain-computer interface (BCI) technology that indirectly measures neuronal activity in the brain's cortex via neuro-vascular coupling. fNIRS works by quantifying hemoglobin-concentration changes in the brain based on optical intensity measurements, measuring the same hemodynamic changes as functional magnetic resonance imaging (fMRI). The light can be used to probe into the tissue of interest, such as the brain, and is able to pass through the scalp, skull, and cerebral cortex. Deoxygenated and oxygenated hemoglobin absorb red and infrared light in different intensities, which, according to the modified Beer-Lambert law, allows for the calculation of the ratio of changes in the hemoglobin concentrations. The ability to objectively observe changes in hemoglobin concentrations is especially useful in brain tissue as regional brain activity utilizes oxygen in the blood (converting oxygenated hemoglobin to deoxygenated hemoglobin); in this way, fNIRS can detect area-specific brain activation patterns. fNIRS technology provides brain region activity specificity (similar to the spatial resolution of fMRI) as well as a sufficient sampling rate (better temporal resolution than fMRI but not as good as EEG), while also being highly portable, less obtrusive, and non-invasive. With enough probes in enough locations, fNIRS can detect these hemodynamic activations across the subject's entire head, thus allowing the determination of cognitive state through the use of pattern classification and data modeling technics such as machine learning.

Despite the advantages of fNIRS over other neurotechnologies, most commercial fNIRS devices remain bulky and difficult to deploy in an operational environment. Many devices also use expensive laser light sources and detectors, making the technology cost prohibitive at scale. Furthermore, current commercial solutions provide neural data outputs that require specialized training to analyze and interpret, rendering them meaningless for the average Warfighter/operator.

To truly exploit neural data for the purposes of supporting Warfighter preparedness estimation, there is a need for a new solution that provides real-time, miniaturized, and resilient fNIRS measurement that is robust to artifacts so that it can be used in challenging, dynamic environments to inform users of their real-time preparedness and cognitive state.

To make new fNIRS technology practical for operational settings, advanced analytics are needed to accurately estimate a user's state and preparedness based on objective data.

The Technical Solution

The aforementioned challenges present an opportunity for the emergence of a new solution for the neural state monitoring of individuals and teams. This solution should provide previously unavailable state assessment information to the users who need it most. The information should be reliable and based on quality data, regardless of the difficult environments in which the system may be employed. Furthermore, the collection of online neural data should not come at the cost of the health and safety of the subject. In short, the optimal solution should provide a complete system rather than simply delivering another wearable device in already crowded market.

In one example embodiment of the state assessment system, called fORE (fNIRS Operational Readiness Estimation system), the system includes three complementary components: (1) a flexible hybrid electronic (FHE) based fNIRS device, (2) an advanced analytics subsystem, and (3) a decision support tool that communicates actionable information to users. One example of embodiment of the fORE solution is illustrated in FIG. 1 as described in detail below.

The state assessment system generally comprises:

fNIRS Device—rugged, portable, unobtrusive sensing device that incorporates FHE technology to maximize compatibility with operational environments; designed with considerations of government grade encryption and intrinsic safety.

Analytics subsystem—advanced data analytics, digital signal processing, and algorithms for rapid characterization of fNIRS data; specifically architected to address the analytic challenges of dynamic environments.

Decision support subsystem—an artificial intelligence (AI)-enabled decision aid developed according to human-centered design principles that communicates actionable information to users regarding the cognitive preparedness of the warfighter and decides and recommends interventions when suboptimal neural states are detected by the system.

fORE, as an example embodiment, is configured to collect the requisite data, appropriately handle those data, and then supply actionable assessments to users.

Difference of Technical Solution from Prior Art

Mission or task preparedness at the individual and team level, and the associated physiological or psychological states, are traditionally analyzed with subjective measurement techniques (e.g., gut feelings or interrogation). In high-stakes environments such as warfare, commercial aviation, heavy machinery operation, medicine, and public safety and first response (e.g., law enforcement), subjective assessments that ultimately prove to be inaccurate can lead to devastating outcomes. For example, imagine being scheduled for surgery with a surgeon who has had no sleep in the past 24 hours, or imagine having your 911 call responded to by an inebriated law enforcement officer. Although these examples are contrived, they clearly accentuate the need to objectively quantify preparedness and fitness-for-duty in high-stakes operational environments.

Existing solutions to this problem rely on subjective estimations of preparedness. The system supports a sensor data agnostic approach allowing for a variety of sensors providing data. Examples of potential data include but not limited to neurological sensors such as fNIRS, EEG; cardiac data, such as heart rate, inter beat interval, heart rate variability, etc.; and an individual's physiological data such as temperature, respiration, galvanic skin response, motion, etc. The technical solution to provide objective estimates of operator states based on available sensor data represents a novel approach.

The Practical Application of the Technical Solution

The system utilizes fNIRS technology and other physiological sensor data to provide an objective estimate of preparedness for a subject. The state assessment system is characterized by superior signal-to-noise ratio (SNR) and sensitivity to detect small hemodynamic changes in humans.

This modeling approach uses machine learning and artificial intelligence (AI)-based techniques as the basis for prediction of the physiological states and may rely on individual data history and trends for each user to more easily and reliably identify suboptimal performance states. Taken together, the analytic strategies will result in both high sensitivity and high specificity in feature extractions for the characterization of preparedness.

The ability to quantify readiness and fitness for duty is a challenging but valuable objective for both military and commercial applications ranging from intel analysts to medical professionals. The disclosed state assessment system provides a holistic technology suite that uses the principles of diffuse optical spectroscopy to quantify and present various physiological and psychological states, such as readiness, attentiveness, workload, and fatigue.

DETAILED DESCRIPTION OF THE INVENTION

As shown in FIG. 1, the state assessment system generally provides a system to sense the physiological conditions of a user at 120, analyze the data to determine a state of the use at 140 and report on the state of the user at 180. Determining the state of the user provides a way to assess the mission readiness and fitness for duty of the user. The sensing may be done with a sensor, the analysis may be done with an analytics subsystem and the reporting may be done with a decision support subsystem.

Data for calibration and use with the state assessment system may be provide by any type of sensor. Examples of suitable sensors include neurobiological (neurological and/or physiological) sensors. One particularly suitable sensor may be an fNIRS device that may be rugged, portable and capable of operating in dynamic settings (e.g., aviation). In military applications, the fNIRS device may integrate with current warfighter equipment and existing operational workflows.

For analysis of the physiological data from the fNIRS device, the state assessment system defines and uses a set of physiological and psychological states of users relevant to assessing mission readiness. The state assessment system uses an experimental protocol to determine relationship between the physiological data and the user states to both calibrate/train the system and to provide assessment data during operational use.

One Example Embodiment of the State Assessment System

Generally, the state assessment system comprises three complementary components: (1) a sensor device; (2) an analytics subsystem; and (3) a decision support subsystem that presents assessments of various physiological and psychological states. In one example embodiment, the sensor may be an fNIRS device that is rugged, portable, miniaturized, and capable of integration with existing equipment. The data processing and analytics suite will allow for conversion of raw fNIRS signals into estimates of individual and team functional states. The decision support subsystem will allow for distributed and real-time assessment of readiness or other physiological or psychological states. Amalgamation of these three products will allow for unobtrusive neurobiological assessment in dynamic environment, which is often not possible with current neurobiological offerings.

Figure 2:
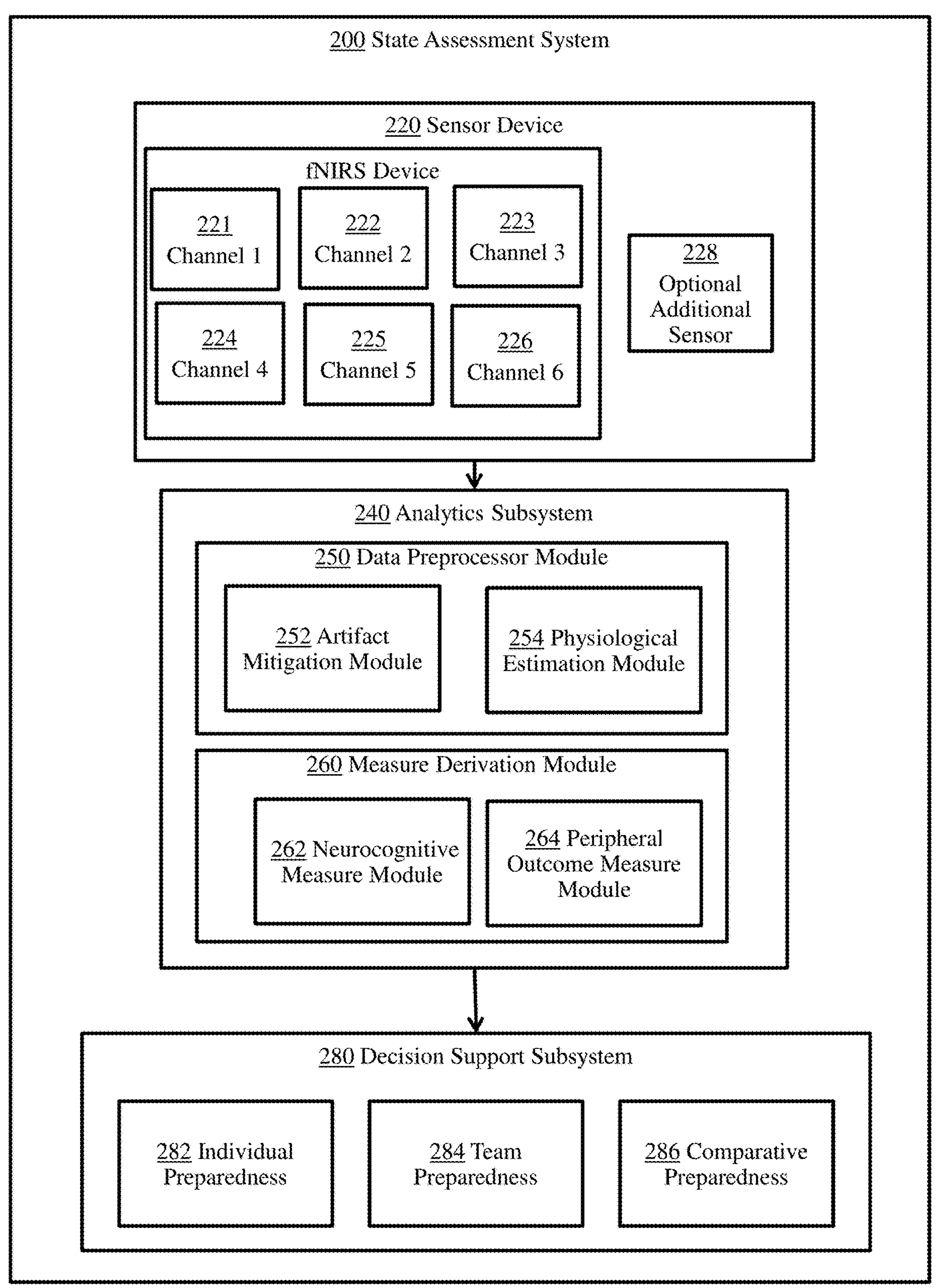
FIG. 2 illustrates a system diagram of one example embodiment of a state assessment system.

FIG. 2 illustrates a system diagram of one example embodiment of a state assessment system. As shown, the state assessment system comprises a sensor device 220, an analytic subsystem 240 and a decision support subsystem 280 used to provide data for objective preparedness estimations.

Sensor Device:

Generally, the sensor device provides a rugged, portable, and unobtrusive tool for data acquisition from the user. As shown in FIG. 2, the sensor device 220 may be an fNIRS device with multiple channels (221-226) or the sensor device may be an optional additional sensor 228 such as a hear rate monitor or a pulse oximeter.

Figure 3A:
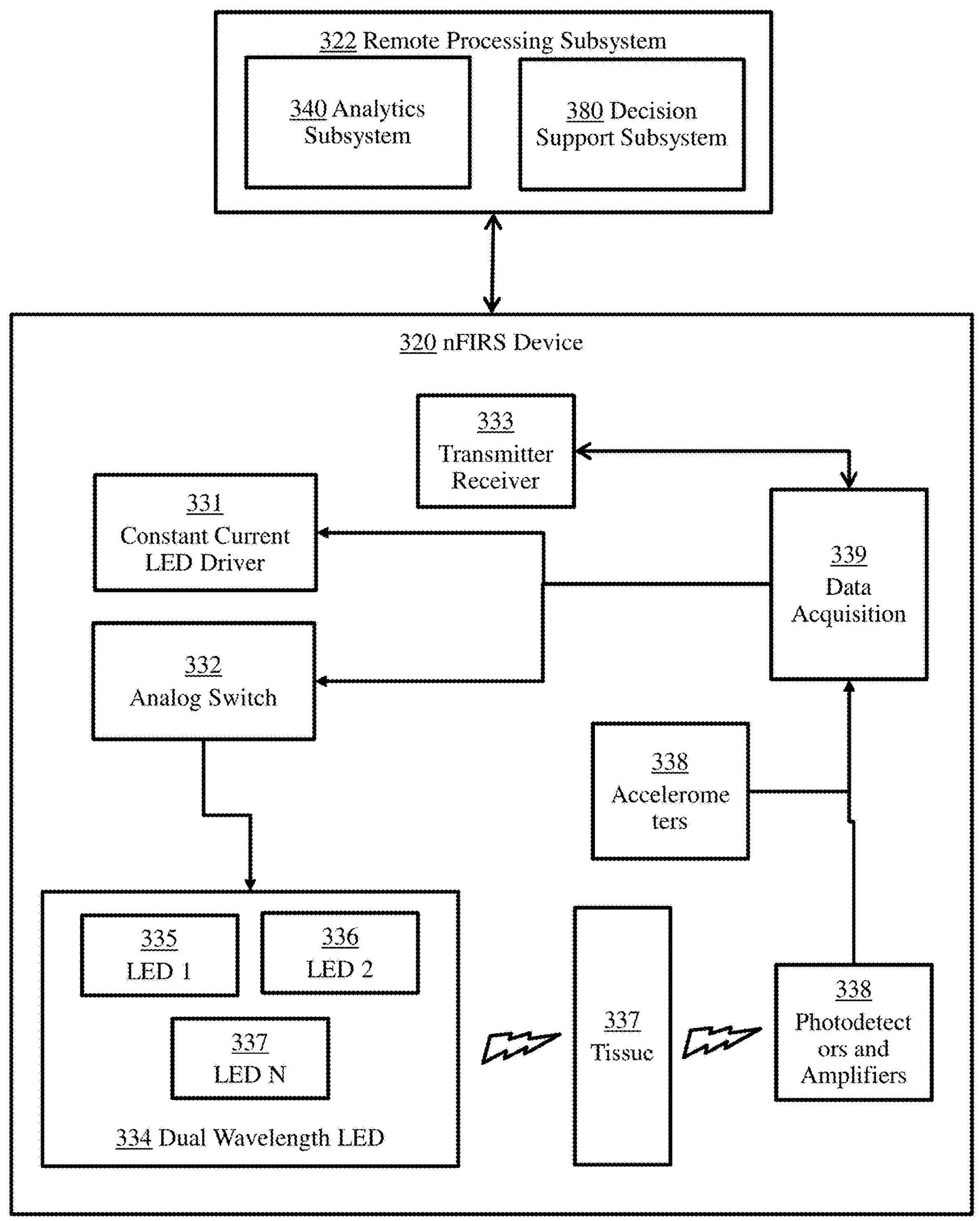
FIGS. 3A-3E illustrate details of an fNIRS device as an example of a sensor with FIG. 3A illustrating a system diagram of an example fNIRS device and FIGS. 3B-3E showing example physical embodiments of fNIRS devices.

One embodiment of the sensor device comprises an integrated fNIRS device capable of capturing neurological data, pulse oximetry, derived heart rate data, and motion data to provide data for objective preparedness estimations. FIG. 3A illustrates a system diagram of one example embodiment of an fNIRS device 320 that communicate with a remote processing subsystem 322. In some embodiments, the fNIRS device is configured to integrate with a pilot's flight helmet while providing both neural and cardiac monitoring in a single device. The fNIRS device is characterized by superior signal-to-noise ratio (SNR) and sensitivity to detect small hemodynamic changes in humans.

Figure 3B:
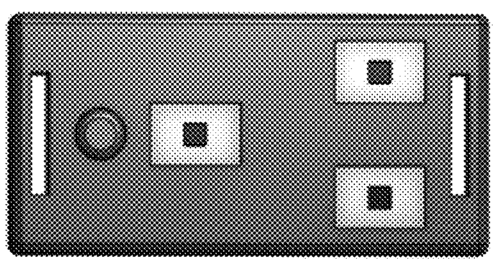

In one example embodiment shown in FIG. 3B, the fNIRS device comprises a head-worn sensor probe that is wired to a separate, small processing unit (e.g., 5 cm×3.5 cm×3 cm). The sensor probe may be made from flexible thermoplastic polyurethane (TPU), and a silicone conformal coating is included in design plans. The device design features a flexible, printed circuit board, integrated accelerometers for better motion artifact processing, programmable gain, and several customizable settings (e.g., LED intensity, channel activation, scanning frequency). The design also incorporates usability benefits such easy donning/doffing, easy repairs (i.e., no special training required), and wireless charging.

Figure 3C:
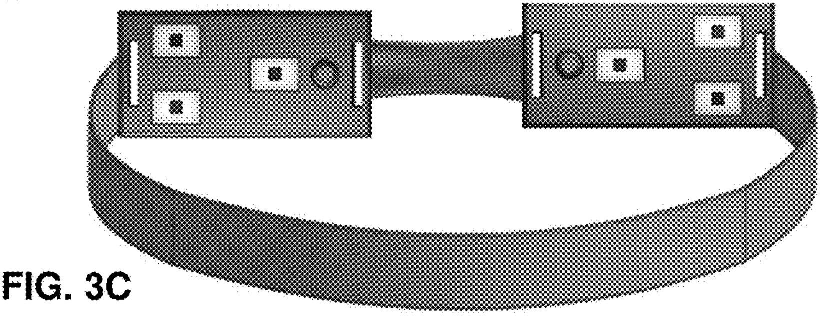

In the example embodiment of the fNIRS device shown in FIG. 3C, the design features two separate sensor pads (one shown in FIG. 3B), each containing one source and three detectors. The near detector is spaced 1 cm from the source, and the far detectors are spaced 3 cm from the source, a spacing that results in optimal SNR. The small probe design features two sensor pads connected by a flexible, adjustable headband; each sensor pad has one source and three detectors. The choice to design two separate sensor pads instead of a contiguous strip across the entire forehead allowed an increase in channel count without impacting comfort. This design is helpful for use with other equipment, as the separate sensor pads aid in solving the issue of unequal contact pressure around sensing locations.

Figure 3D:
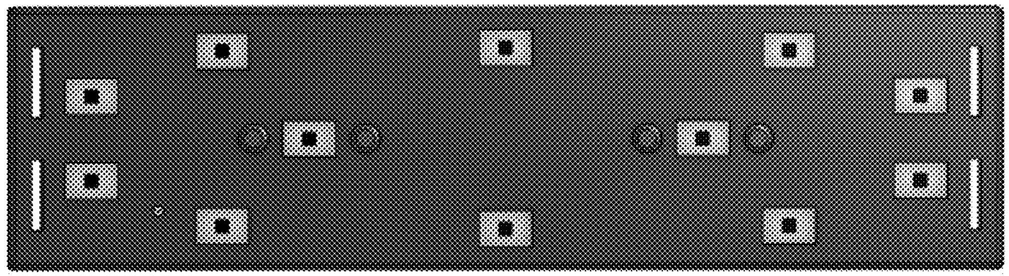

The example embodiment of the fNIRS device shown in FIG. 3D is a larger, single sensor pad, with 4 sources and 12 detectors, providing twice the number of channels compared to the small design concept. This sensor probe would provide more neural coverage and better redundancy in the event of hardware or contact failure at a particular detector site.

Figure 3E:
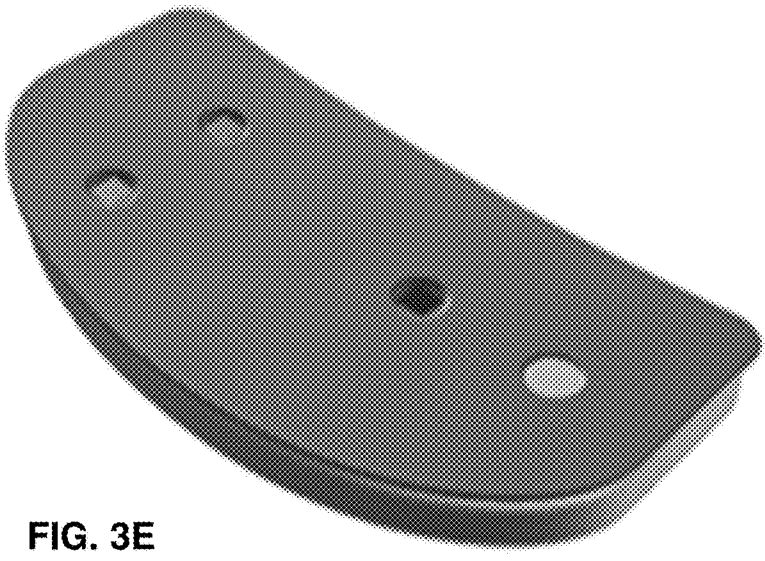

The example embodiment of the fNIRS device shown in FIG. 3E is a slim and lightweight form factor made of flexible material and may use utilize disposable adhesives to adhere the sensor in the appropriate location, without the added bulk of adjustable straps. Accelerometers may also be incorporated into the device to help monitor physical activity. The processing of accelerometer data is well established for assessing physical activity and can provide multiple inputs to assessment models. This will allow the state assessment system to further distinguish user states, characterize data quality, and contextualize neural information.

Analytics Subsystem—Data Preprocessing Module:

Generally, the analytics subsystem provides advanced analytic strategies and algorithms for processing and characterizing neurobiological data and mapping that neurobiological data to cognitive states of individuals and teams. The analytics subsystem generally uses the change in HbO concentration resulting from neural activity and the concept of hemodynamic coupling to define a relationship of neural activity to cognitive states. With this relationship defined, the state assessment system is able to then determine cognitive states based on data obtained by the fNIRS device.

As shown in FIG. 2, the analytics subsystem 240 may comprise a data preprocessor module 250 and a measure derivation module 260. The data preprocessor module 250 generally filters the raw data for use with other system components with the artifact mitigation module 252 and estimates physiological measures with the physiological estimation module 254. The measure derivation module 260 generally determines measures based on the physiological estimates. Measures determined include neurocognitive (e.g., state) measures by the neurocognitive measure module 262 and other measures by the peripheral outcome measure module 264.

Figure 4:
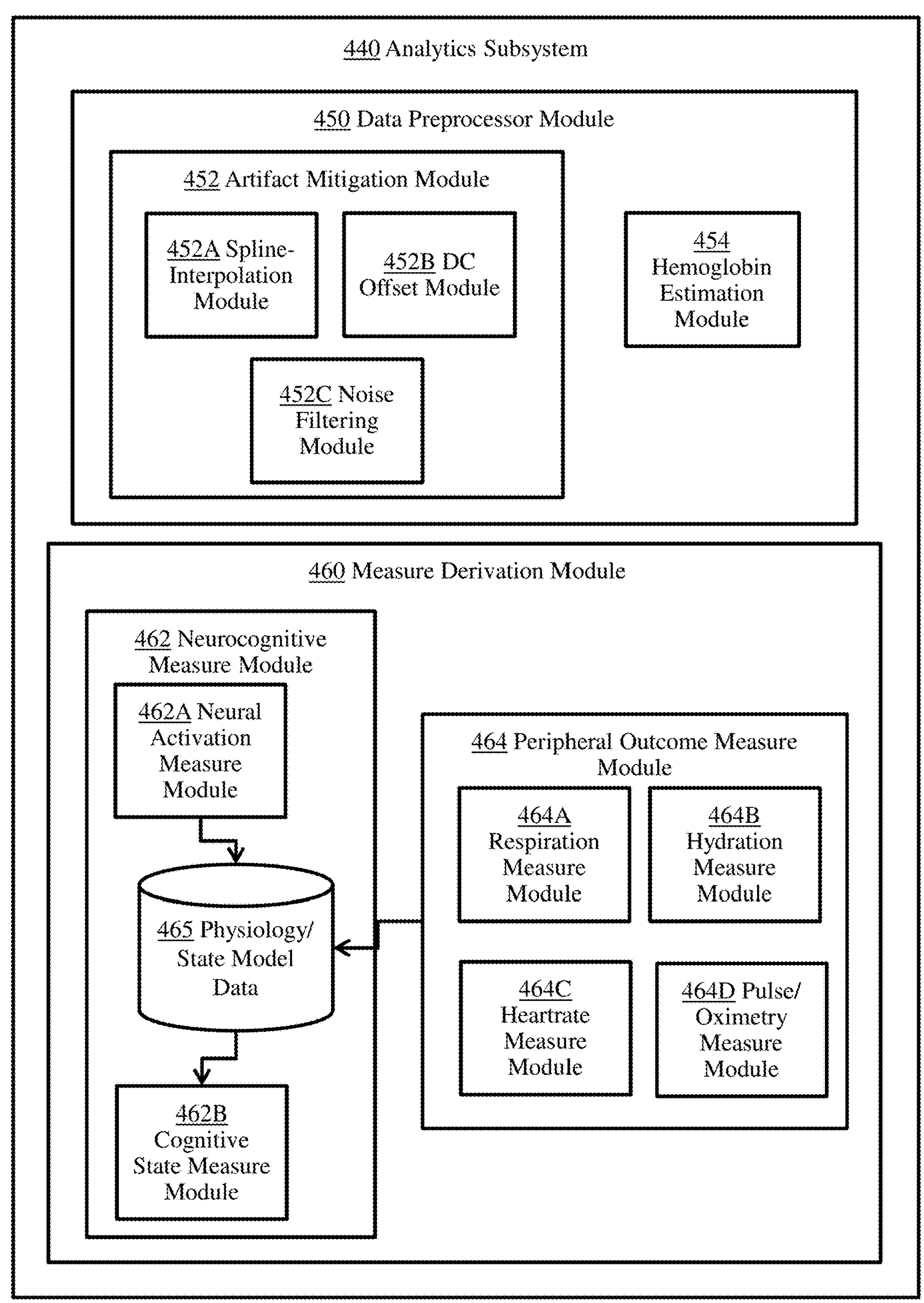
FIG. 4 illustrates a system diagram of one example embodiment of an analytics subsystem.
Figure 5:
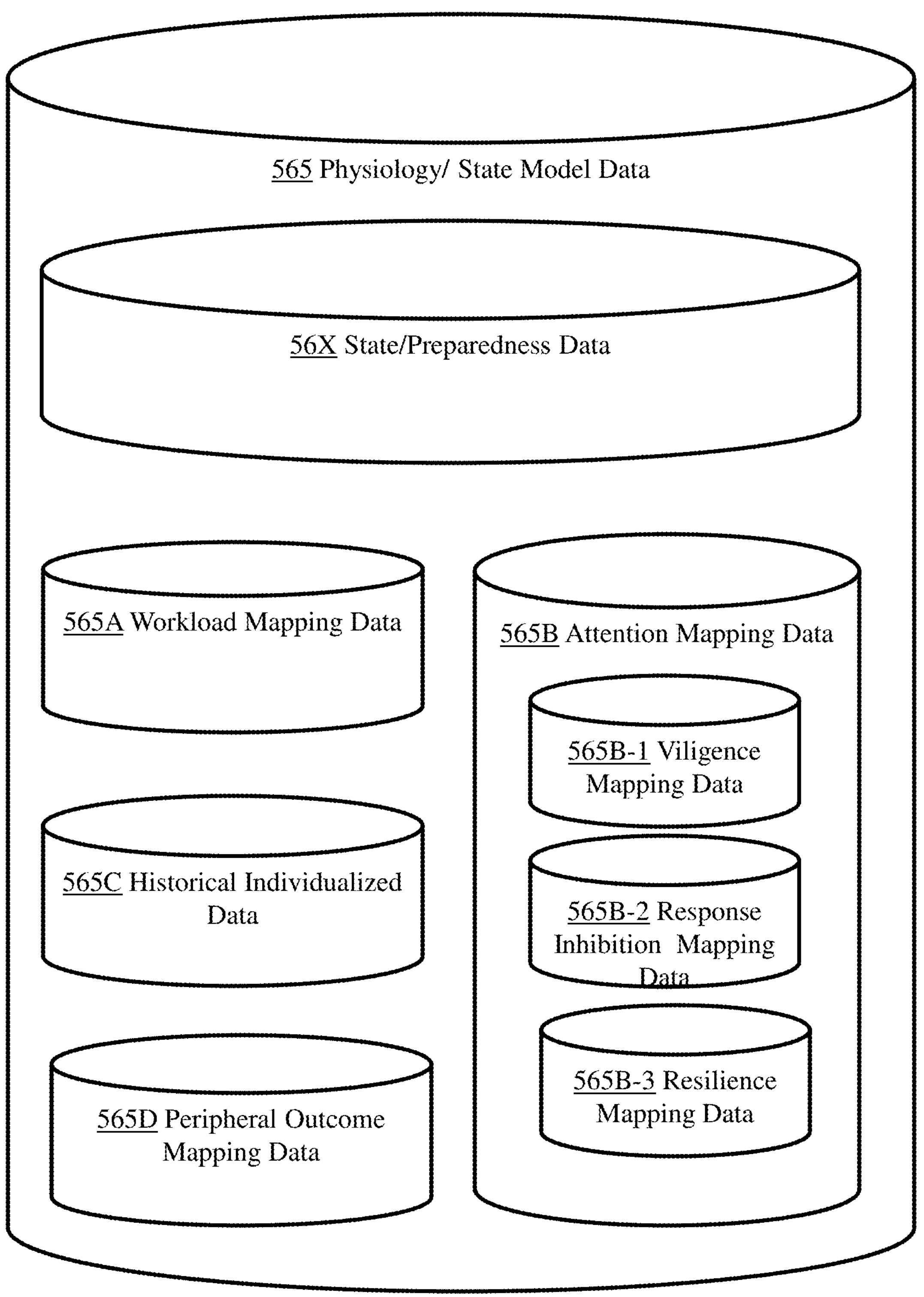
FIG. 5 details example components of the physiology/state model data.

FIG. 4 shows more details of the analytics subsystem 440. In one example embodiment, raw data received from the fNIRS device includes voltage values corresponding with light intensity recorded from two sensors (10 mm=NEAR; 30 mm=FAR) during three types of stimulation (760 nm, 840 nm, and OFF) for a total of six channels. Processing with the analytics subsystem 440 takes place in two stages: (1) preprocessing, including artifact mitigation and derivation of estimated hemoglobin concentrations with the data preprocessor module 450, and (2) derivation of real-time neurocognitive and peripheral outcome measures with the measure derivation module 460.

Preprocessing—Missing Data: Missing data may be spline-interpolated with the spline-interpolation module 452A. Values exceeding+/−five standard deviations (SD) from the mean of a sliding 60-second window are treated as missing data and interpolated; this process is repeated until all values are within 5 SD. Any stretches of data longer than 1000 ms wherein values do not change are also treated as missing data and interpolated.

Preprocessing—DC Offset: Data may also be gently filtered (bandpass; 0.01-5.00 Hz; bidirectional Butterworth Infinite Impulse Response [IIR]; order=5) to eliminate DC offset, slow drifts, and high frequency noise. This may be performed with the DC Offset Module 452B.

Preprocessing—Noise Filtering: For both NEAR and FAR sensors, OFF channels are linearly regressed from the two infrared channels and then discarded with the noise filtering module 452C. Under ideal conditions, the OFF channels would be a flatline of zeros. Practically speaking, the OFF channels contain hardware noise and artifacts from sources such as ambient light. Regressing these from the infrared channels reduces variance that is not correlated with signals of interest.

Preprocessing—Further Filtering: Further filtering will take place in outcome-specific processing modules; because downstream needs differ, depending on the signal of interest, including neural, cardiac, and respiratory information, the passband is kept broad at this stage.

Preprocessing—Hemoglobin Estimation: The processed data are subjected to the modified Beer-Lambert Law (MBLL) transformation to calculate relative (to a baseline) concentrations of oxy-hemoglobin (HbO) and deoxy-hemoglobin (HbR) at the NEAR and FAR sensors. Note that at the FAR (30 mm) sensor is the signal likely to include a neural component. Hemoglobin estimation is determined at the hemoglobin estimation module 454.

Analytics Subsystem—Measure Derivation Module:

Referring to FIG. 2, the measure derivation module 260 generally determines the state of the user with the neurocognitive measure module 262 given the physiological estimates from the date preprocessor module 250. The state of the user may also be determined with other measures such as measures from the peripheral outcome measure module 264.

Referring to FIG. 4, the cognitive state measure from the cognitive state measure module 462B is generally based on the relationship of neural activation measures to the cognitive state measures. The neural activation measures are determined with the neural activation measure module 462A and the relationship of those measures to cognitive state are defined by the physiology/state model date 465. Given a neural activation measure, a cognitive state measure can be determined based on the physiology/state model.

Neural activation measures are determined by measuring hemoglobin concentration at specific locations in the brain. This is analogous to that commonly done in whole-brain functional magnetic resonance imaging (fMRI) research, except that for fNIRS, the probes should be placed strategically on the head to measure the locations of interest in the cortex of the brain. Neural activation measures are derived real-time from sensor data (e.g., fNIRS channels for NEAR and FAR; HbO and HbR. Neural activation is inferred from the HbO-FAR data based on the phenomenon of hemodynamic coupling. Hemodynamic coupling describes the change in HbO concentration resulting from neural activity. Specifically, the hemodynamic response is thought to be driven by glial cells in response to the metabolic cost of firing action potentials. In embodiment, because hemodynamic responses to neural activity are relatively slow, data are more aggressively filtered (lowpass; 0.10 Hz; bidirectional Butterworth IIR; order=5). A source-detector separation of 10 mm is generally insufficient to capture neural responses but can capture many of the same signals of non-interest (e.g., from pulse, respiration, or motion) as a 30 mm separation. For this reason, NEAR channel data are regressed out of FAR channel data and discarded. Because the hemodynamic response lags neural activity by about 6 seconds, data from 6 seconds prior to the current time point are taken as a measure of neural activation.

The physiological/state model data generally includes trained data or algorithms that define an objective relationship between the neural activation measure and cognitive state measures. Neural activation measures, as indicated by hemoglobin concentrations, over time may be used to determine cognitive state through the use of one of many machine learning algorithms including, but not limited to, artificial neural networks, support vector machines, k-nearest neighbors, etc. Such algorithms can be applied to define these relationships by defining them as physiological/state model data to match the outcomes of experimental data (i.e., "training data").

For the neurocognitive measures, cognitive state measures may be defined by the following data or any combination of this data:

- Attention data, which may be defined as sustained attention (vigilance), executive control (response inhibition), and focus (resilient against distractions).
- Workload data, which may be defined as the ability to hold, manage, and/or update many pieces of information in memory for the purpose of performing well on a task.
- Historical individualized data, which may be defined as historical data for neural activation measures, attention measures and workload measures of a user or a group of user that may be used to individualize the physiological/state model for that user or group.

Other potential cognitive state measures may include motor learning, stress, task engagement, fatigue, decision making, expertise and functional connectivity.

In some embodiments, the cognitive state measure may also be determined or refined by peripheral outcome measures. Referring to FIG. 4, these peripheral outcome measures may include measures determined from a respiration measure module 464A, a hydration measure module 464B, a heartrate measure module 464C or a pulse/oximetry measure.

In some embodiments the cognitive state measure, and other system measures, may be used to determine measures such as preparedness.

In some embodiments the workload data may be further calibrated by the use of surveys consistent with the NASA task load index (NASA TLX).

Decision Support Subsystem:

Generally, the decision support subsystem provides a tool for supporting decision making in operational contexts, exploits the processed neural data to deliver actionable information to users, and decides and recommends intervention strategies when suboptimal neural states are detected. The decision support platform may recognize instances in which suboptimal states are detected, decide on an appropriate intervention, and deliver it to the user, all while presenting real-time physiological information via human-centered design principles.

Figure 7:
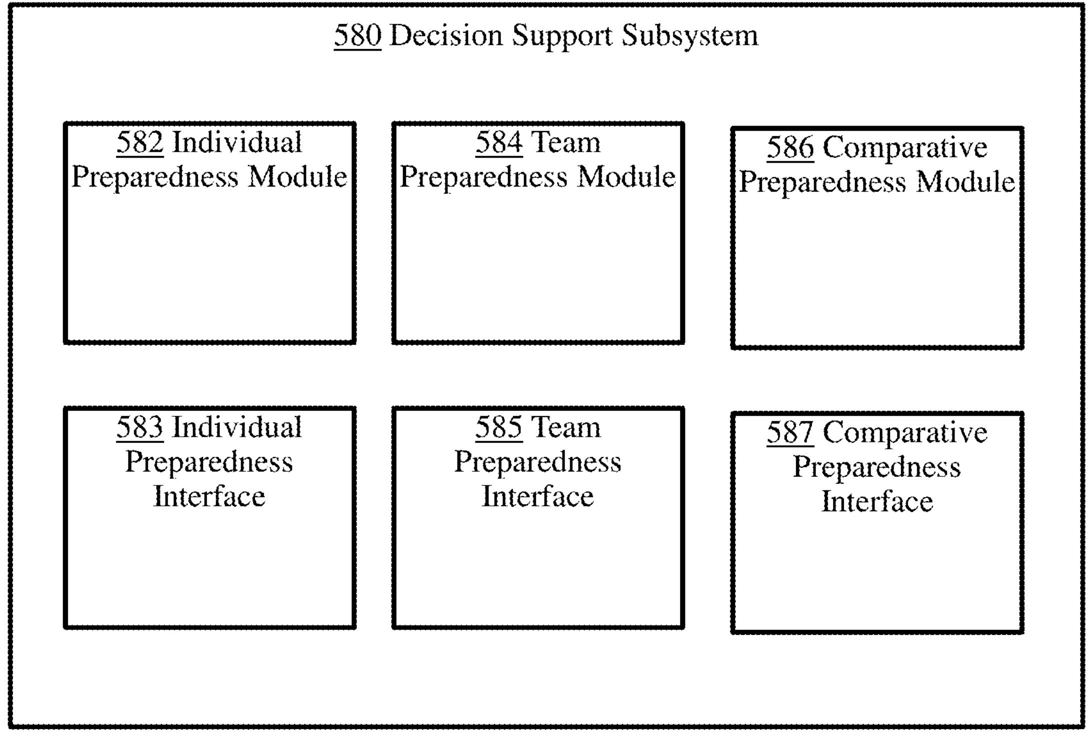
FIG. 7 illustrates components of an example embodiment of the decision support subsystem.

As shown in FIG. 7, the decision support subsystem 580 may include different modules to determine measures to communicate through different interfaces. For example, the decision support subsystem 580 may be a user interface (UI) that provides actionable data for the following realistic activities:

- Determine an assessment of an individual's overall preparedness state with the individual preparedness module 582;
- View the assessment of an individual's overall preparedness state with an individual preparedness interface 583, with the ability to drill down to learn more about the specifics of this assessment;
- Determine an assessment of a team's preparedness state with the team preparedness module 584;
- View the assessment of the team's preparedness state with the team preparedness interface 585;
- Determine a comparative assessment of individuals' preparedness state with a comparative preparedness module 586; and Provide a comparison of individuals' states to support team selection or mission assignment with a comparative preparedness interface 587.

The decision support subsystem may also be configured to support pre-mission crew planning decisions by providing a team-of-teams-level view with global details about the team. This functionality makes it possible for current state information to influence possible changes to crew and/or crewmembers prior to a mission start. For example, an aircraft crewmember status page of the UI may provide a snapshot of an entire selected crew in one area and allow for one crewmember's status to be viewed in detail in another area. Selecting an individual provides access to their real-time health and state information. The status panel may show the crewmember's image, name, crew position, flight certifications, and physical location within the aircraft. The health and state information could allow for various interventions. For example, crewmembers could utilize the biofeedback and potentially see positive results given reports that awareness of one's physiology is sufficient to improve maladaptive states. The team also envisions the UI supporting interventions via task-reallocation strategies. If a crewmember enters a maladaptive state, it might be possible to shuffle tasking among the crew to alleviate task burden or to ensure that critical tasking is handled by a crewmember in an optimal state.

The decision support subsystem may also be configured to deliver key information and allow for user-driven exploration of the state assessment data.

Analytics Subsystem—Determining the Physiology/State Model for Attention Data:

To determine the physiological/state model, a series of training activities can be run to create the initial data models. By running a series of tests using known or expected cognitive states over a period of time, and also determining the neural activation measures over the same time, one or more physiological/state model may be determined. The model may be determined through the use of one of many machine learning algorithms including, but not limited to, artificial neural networks, support vector machines, k-nearest neighbors, etc. Such algorithms can be applied to define these relationships by defining them as physiological/state model data to match the outcomes of the tests (i.e., "training data").

To determine these relationships, participants may be fitted with the sensor (e.g., fNIRS) device, and be asked to undergo a task (or tasks or tests) intended to induce a range of levels of to-be-investigated cognitive constructs (e.g., workload or attention). Event markers time-locked to changes in these levels throughout the task should correspond with the times when the state assessment system detects a change in state levels. Participants will complete the task while state assessment system monitors their brain activity and generates assessments of cognitive state levels.

To determine attention mapping data, standardized cognitive tasks with known attention measures may be used to create the mapping/training data. For attention mapping data, this may be broken down into three measures: sustained attention (vigilance), executive control (response inhibition), and focus (resilient against distractions).

Figures 6A, 6B, 6C, 6D:
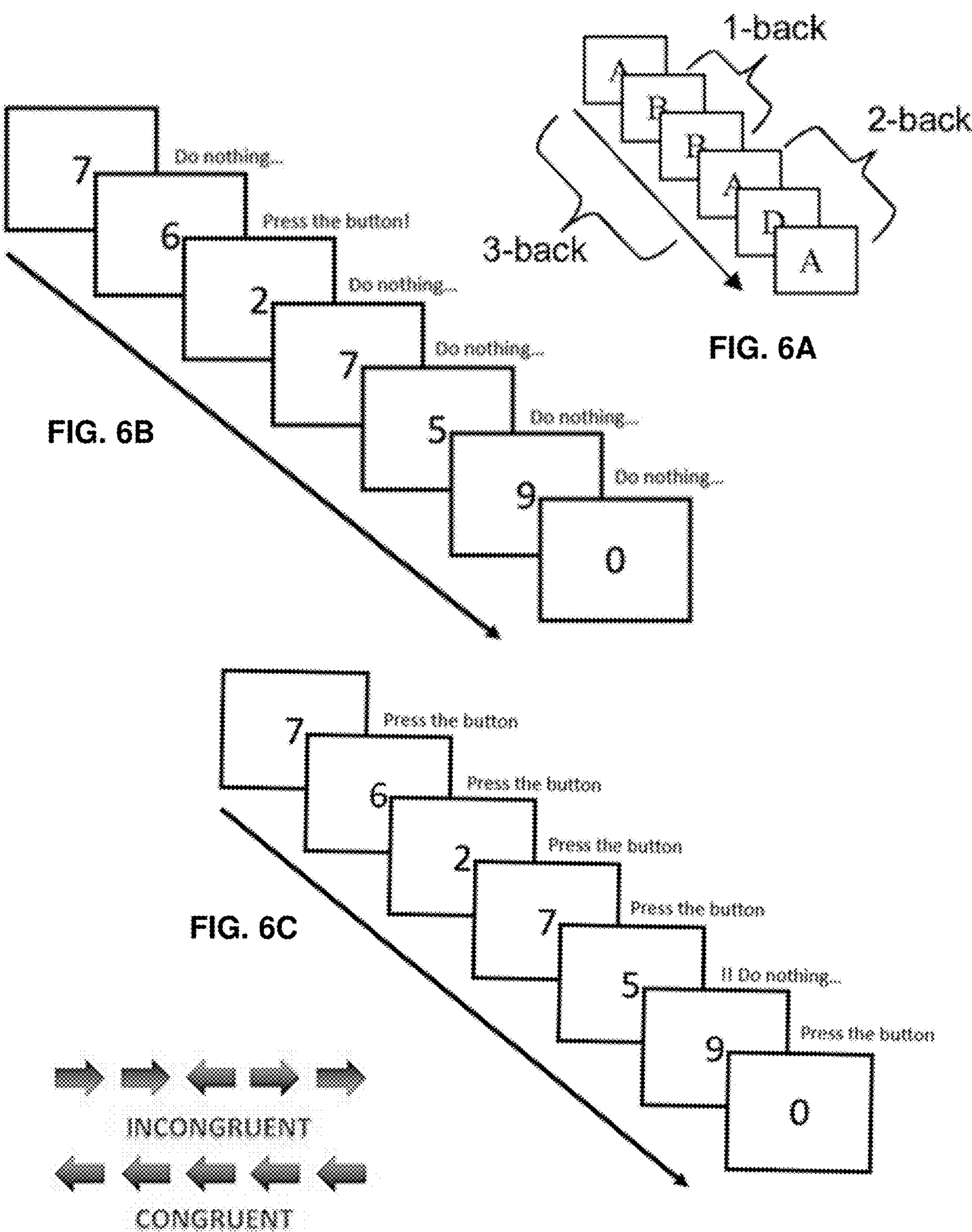
FIGS. 6A-6D show example testing methods to calibrate and train the physiology/state model.

For sustained attention (vigilance) and executive control (response inhibition), a Continuous Performance Task (CPT) may be performed. For a CPT, participants are asked to view stimuli as they are presented one at a time and to respond in a very specific way—either pressing a button or restraining from pressing a button—whenever they see the target stimulus (see FIG. 6B). Participants may complete 10 blocks each of two versions of this task: one version being a Vigilance Task and the other version being a Sustained Attention to Response Task (SART). For either version, stimuli and trials are similar: single digit, randomized presentations of the numbers 0 to 9 for 500 ms each, followed by a fixation cross for 500 ms, and an intertrial blank ~400 ms. For the Vigilance Task, as shown in FIG. 4B, participants will be asked to respond as soon as they see a target number (e.g., pressing a button only when they see the number 6). Alternatively, for the SART version of this task, as shown in FIG. 6C, participants will be asked to respond to every number with a button press with the exception of the target number (e.g., don't press when you see the number 5).

Prior to starting each version of the task, participants will receive 5 minutes of instructions and practice. Blocks will contain 30 trials each. Each block will start with 5 s of instruction, informing participants which version of the task they are about to complete. At the end of each block, a cross will be displayed for 15 s during which participants will be asked to relax to ensure that hemoglobin levels return to baseline. As with the n-back task, we will exclude these return-to-baseline periods from our analysis as they are strongly influenced by the previous hemodynamic responses. For a half of the blocks, an additional 30 s of the resting cross will be displayed to have data periods with no activity to be used as "relax" blocks. These periods are used with true relax signals for analysis (instead of periods in which HbO and HbR returned to baseline). At the mid-point, a 150 s break will be included during which the participants can drink or chat. The entire CPT task is expected to have a duration of ~34 min (5 minutes of instruction/practice, 20 blocks of 62 s, 10 relax blocks of 30 s, and 150 s in the middle). Blocks will pseudo-randomized across participants. Accuracy will indicate the proportion of trials correctly responded to.

Sensor data will be recorded continuously during these tasks. State assessments will be evaluated with respect to these attention conditions (vigilance, SART, relax) and performance scores.

With the data obtained from this testing, an objective relationship between the neural activation measures and attention measures may be determined through machine learning algorithms including, but not limited to, artificial neural networks, support vector machines, k-nearest neighbors, etc. This objective relationship may be defined as attention mapping data, vigilance mapping data, response inhibition mapping data or as algorithms in the physiology/state model data.

For focus (resilience to distractions), an Attention Network Task (ANT) may be performed. In each trial of the task, as shown in FIG. 4D, there will be a fixation cross at the center of the screen for 500 ms; then, a blank will be presented for 100 ms; followed by the stimulus which will remain on screen for up to 1000 ms or until the participant responds. Stimuli are composed of 5 arrows: two flankers on either side of a center arrow. It is the participant's task to press a button as soon as possible to indicate the direction that the center arrow is facing, left or right. Sometimes the flanker arrows will face in the same direction as the center arrow (congruent trials) while, at other times, the flanker arrows will all face in the opposite direction (incongruent trials); see FIG. 6D. There will be a short intertrial interval of ~500 ms.

Prior to starting this task, participants will receive 5 minutes of instructions and practice. Participants will complete 10 blocks of each condition (congruent and incongruent). Blocks will contain 28 trials each. Blocks will be randomly ordered per participant. At the end of each block, a cross will be displayed for 15 s during which participants will be asked to relax to ensure that hemoglobin levels return to baseline. As with the other tasks, we will exclude these return-to-baseline periods from our analysis as they are strongly influenced by the previous hemodynamic responses. For a half of the blocks, an additional 30 s of the resting cross will be displayed to have data periods with no activity to be used as "relax" blocks. We intentionally use these periods with true relax signals for our analysis (instead of periods in which HbO and HbR returned to baseline). At the mid-point, a 150 s break will be included during which the participants can drink or chat. The entire ANT is expected to have a duration of ~33-39 min (5 min instruction/practice, 20 blocks of 62-79 s, 10 relax blocks of 30 s, and 150 s in the middle). Accuracy will indicate the proportion of trials correctly responded to.

Sensor data will be recorded continuously during this task. State assessments will be evaluated with respect to focus conditions (congruent, incongruent, relax) and performance scores.

With the data obtained from this testing, an objective relationship between the neural activation measures and focus measures may be determined through machine learning algorithms including, but not limited to, artificial neural networks, support vector machines, k-nearest neighbors, etc. This objective relationship may be defined as attention mapping data, resilience mapping data or as algorithms in the physiology/state model data.

Analytics Subsystem—Determining the Physiology/State Model for Workload Data:

The cognitive construct of workload as the ability to hold, manage, and/or update many pieces of information in memory for the purpose of performing well on a task. To determine this type of workload mapping data, standardized cognitive tasks may also be used to create the mapping/training data. For workload mapping data, an n-back task may be used. In the n-back task, participants must continuously remember the last n of a series of rapidly displayed stimuli. When the current stimulus matches the $n^{th}$ stimulus before it, we call the current stimulus a target and the $n^{th}$ stimulus back the reference. Participants are asked to react (press a button) when they notice targets (i.e., go/no-go responding); see FIG. 6A. The task is easiest in the 1-back condition, where the participant is only monitoring for when a stimulus matches the ONE before it. The task becomes more difficult at the 2-back condition, where the participant has to always remember the two prior stimuli and match the one that is TWO back with the currently displayed one (and continuously update and match with each new stimulus). Understandably, the task is most difficult in the 3-back condition. Performance in this task can be evaluated by measuring the proportion of missed targets or false alarms (when participants either do not press the button for a target or do press the button during a non-target stimulus).

The test may be run with 10 blocks each of 1-, 2-, and 3-back tasks. Each block will contain 3±1 targets. Each block will include 5 s of instruction, informing participants which task (1-, 2- or 3-back) they are about to complete. The block will present a new stimulus every 2 s. Every stimulus will be displayed for 500 ms, then the screen will remain blank for the remaining 1.5 s. A total of 20 trials (stimulus+blank) will be presented during every block. At the end of each block, a cross will be displayed for 15 s during which participants will be asked to relax to ensure that hemoglobin levels return to baseline. We will exclude these return-to-baseline periods from our analysis as they are strongly influenced by the previous hemodynamic responses. For a third of the blocks, an additional 30 s of the resting cross will be displayed to have data periods with no activity to be used as "relax" blocks. These periods with true relax signals are used for analysis (instead of periods in which HbO and HbR returned to baseline). At the mid-point, a 150 s break will be included during which the participants can drink or chat. The entire n-back task is expected to have a duration of ~43 min (5 minutes of instruction/practice, 30 blocks of 60 s, 10 relax blocks of 30 s, and 150 s in the middle). The order of the different n-back conditions will be pseudo-randomized across participants.

Sensor data will be recorded continuously during this task. State assessments will be evaluated with respect to these workload conditions (1-back, 2-back, 3-back, relax) and performance scores.

With the data obtained from this testing, an objective relationship between the neural activation measures and workload measures may be determined through machine learning algorithms including, but not limited to, artificial neural networks, support vector machines, k-nearest neighbors, etc. This objective relationship may be defined as workload mapping data or as algorithms in the physiology/state model data.

In addition to determining workload mapping data, this workload data may be further calibrated. For example, at the end of each task, participants may be asked to answer the NASA Task Load Index (TLX) to define a measure to compare to the other workload data. The NASA task load index (NASA TLX) is a tool for measuring and conducting a subjective mental workload (MWL) assessment. It allows you to determine the workload of a participant while they are performing a task. It rates performance across six dimensions to determine an overall workload rating. The six dimensions are as follows:

- Mental demand: How much thinking, deciding, or calculating was required to perform the task.
- Physical demand: The amount and intensity of physical activity required to complete the task.
- Temporal demand: The amount of time pressure involved in completing the task.
- Effort: How hard does the participant have to work to maintain their level of performance?
- Performance: The level of success in completing the task.
- Frustration level: How insecure, discouraged, or secure or content the participant felt during the task.

Each of the above subscales are presented to the participants either during or after the experimental task. They are asked to rate their score on an interval scale ranging from low (1) to high (20). The TLX also employs a paired comparisons procedure. This involves presenting 15 pairwise combinations to the participants and asking them to select the scale from each pair that has the most effect on the workload during the task under analysis. This procedure accounts for two potential sources of between-rater variability: differences in workload definition between the raters and differences in the sources or workload between the tasks.

The subscales are given to the participants either during or following their experimental tasks. The participants may self-rate on a scale of 1 (low) to 20 (high) using 15 pairwise combinations designed to elicit from the participants the pair that has the greatest effect on workload while performing the task.

Analytics Subsystem-Peripheral Outcome Measures:

In some embodiments, heart rate data may be included in the physiology/state model data. Heart rate (HR) may be inferred from all non-OFF channels of the sensor based on the method in. Pulsatile expansion and contraction of surface blood vessels cause detectable changes in signal intensity. Though this pulsatile effect can be seen as an artifact detrimental to neural activity estimation, it can itself be a useful signal in its own right (for measuring heart rate) and is easily filtered out from the much slower hemodynamic signal. First, the power spectral density (PSD) is calculated for each channel using the fast Fourier transform. Next, channels whose PSD contains a local maximum exceeding a certain threshold (two standard deviations [SD] above the mean for the window) within a typical yet liberal HR range (0.7 Hz to 2.0 Hz in our case) are selected for further analysis. Data are then upsampled to 100 Hz to increase the precision of interbeat interval detection and bandpass filtered to the HR range mentioned above. Peak (latency and value) are extracted with a 300 ms minimum spacing and interpeak intervals are calculated. Intervals three SD longer than the mean are interpreted as missing beats, and missing beats are imputed, bisecting the interval (e.g., a 2800 ms interval will be replaced with two consecutive 1400 ms intervals. This process is iterated until all missing beats are imputed. Instantaneous HR for each channel is calculated as the reciprocal of the most recent interpeak interval, and this time course is upsampled to 20 Hz. With the HR time course for each channel, the instantaneous HR can be calculated by taking the median across channels. Additionally, the HR signal may be subjected to a 0.3 Hz lowpass filter.

In some embodiments, respiration rate data may be included in the physiology/state model data. Respiration rate may be calculated from the derived HR described above. First, the inverse would be taken in order to give a time course of interbeat intervals. Respiration would then be measured as the inverse of the peak frequency in the (0.1-0.4) range, calculated in a sliding 15-second window.

In some embodiments, hydration and pulse/oximetry data may be included in the physiology/state model data.

Figure 8:
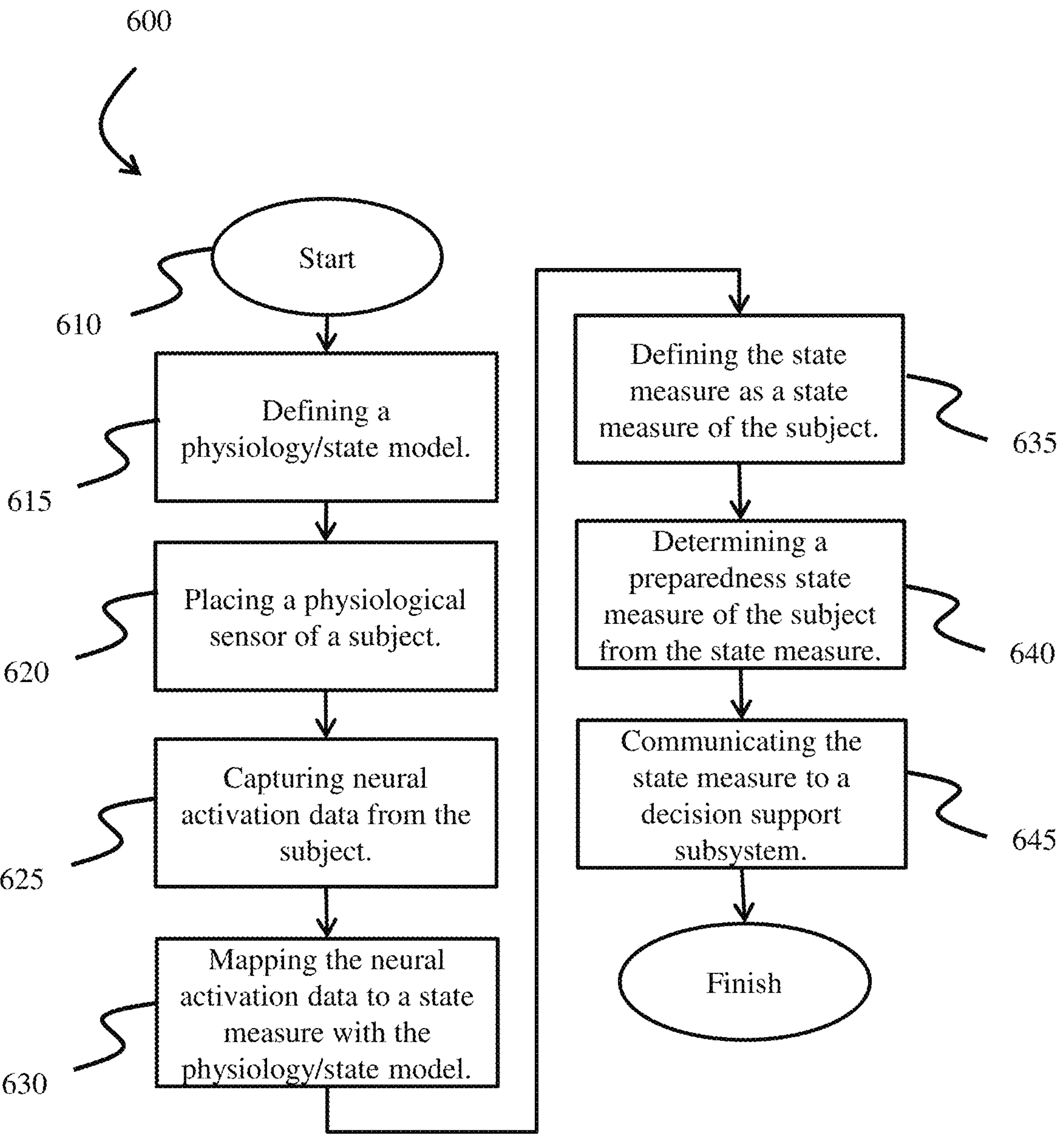
FIG. 8 illustrates a process diagram of an example embodiment of using the state assessment system.

One Embodiment of Methods of Using the State Assessment System:

One example embodiment of using the state assessment system is shown in FIG. 8.

Starting at 610, the physiology/state model is defined at 615. The physiology/state model may be predefined or it may need to be determined/trained.

At 620 a physiological sensor is placed on a subject to measure physiological data.

At 625, neural activation data is captured from the subject.

At 630, the neural activation data is mapped to a state measure with the physiology/state model.

At 635, the state measure mapped to in step 630 is used to define the state measure of the subject.

At 640, optionally, a preparedness state measure of the subject may be determined from the state measure.

And at 645, the state measure is communicated to the decision support subsystem.

One Embodiment of the State Assessment System in Operation:

One example embodiment of use of the disclosed state assessment system comprises and operators control of multiple unmanned vehicles. In this example, an operator is required to control multiple unmanned aerial or underwater vehicles (UAVs or UUVs) in a path planning, obstacle avoidance, surveillance task. Unmanned vehicles (UVs) travel along planned paths toward their target. Upon arrival, a payload task is spawned, requiring the operator to search for target. After completing the payload task, the UV is assigned a new target and the process (of navigation followed by visual search upon arrival) repeats. The operator's navigation planning task involves rerouting UVs to avoid threat areas and reassigning UVs to targets when poor assignments are returned by an automated planner. Generating additional urgency for the operators, targets have time limits on them; operators must use all the UVs as their disposal as efficiently as possible to reach as many targets as they can before they expire. Other factors may also come into play such as fuel supply or battle damage.

Conditions the operator may face in performing their tasks include various levels of automation (i.e., manual, medium, and high) across varying levels of task load (for example, 3 UAVs and 12 Hazards-low, 6 UAVs and 24 Hazards-high). Automation may be impacted by how participants set the paths of the UAVs to targets (i.e., manually, offered three potential paths, fully automated) and by the reliability of the automation (i.e., providing correct suggestions only a variable amount of the time). Task load may also be impacted by the number of UAVs (up to 6) and number of hazards (typically 3-4 per UAV). Throughout the mission, participants will accumulate points towards their performance score based on their accuracy.

fNIRS data will be recorded continuously during this task, for the length of the task. The analytics subsystem will receive the fNIRS data and use it to determine the cognitive state of the operator. The cognitive state determined may be used to determine a level of automation to provide task assistance to the operator.

An additional operational use case may include pre-mission assessments where the operators may be tested prior to a mission in order to determine the operator's preparedness before being assigned a mission.

An additional operational use case may include during-mission assessments where operators may be tracked real-time and mission tasks may be changed based on the operator's real-time preparedness or multiple operators may be tracked on a team mission and mission tasks may be reallocated based on the preparedness of operators compared to each other.

An additional operational use case may include using historical data of an operator to determine pre-mission or during-mission assessments of an operator's preparedness.

One Embodiment of a State Assessment System Implemented in a Software Program Product Executed by a Processor Based System:

As will be readily apparent to those skilled in the art, one embodiment of the state assessment systems and methods can be embodied in hardware, software, or a combination of hardware and software. For example, a computer system or server system, or other computer implemented apparatus combining hardware and software adapted for carrying out the methods described herein, may be suitable. One embodiment of a combination of hardware and software could be a computer system with a computer program that, when loaded and executed, carries out the respective methods described herein. In some embodiments, a specific use computer, containing specialized hardware or computer programming for carrying out one or more of the instructions of the computer program, may be utilized. In some embodiments, the computer system may comprise a device such as, but not limited to a digital phone, cellular phone, laptop computer, desktop computer, digital assistant, server or server/client system.

Computer program, software program, program, software or program code in the present context mean any expression, in any language, code or notation, of a set of instructions readable by a processor or computer system, intended to cause a system having an information processing capability to perform a particular function or bring about a certain result either directly or after either or both of the following: (a) conversion to another language, code or notation; and (b) reproduction in a different material form. A computer program can be written in any form of programming language, including compiled or interpreted languages, and it can be deployed in any form, including as a stand-alone program or as a module, component, subroutine, or other unit suitable for use in a computing environment.

Figure 9:
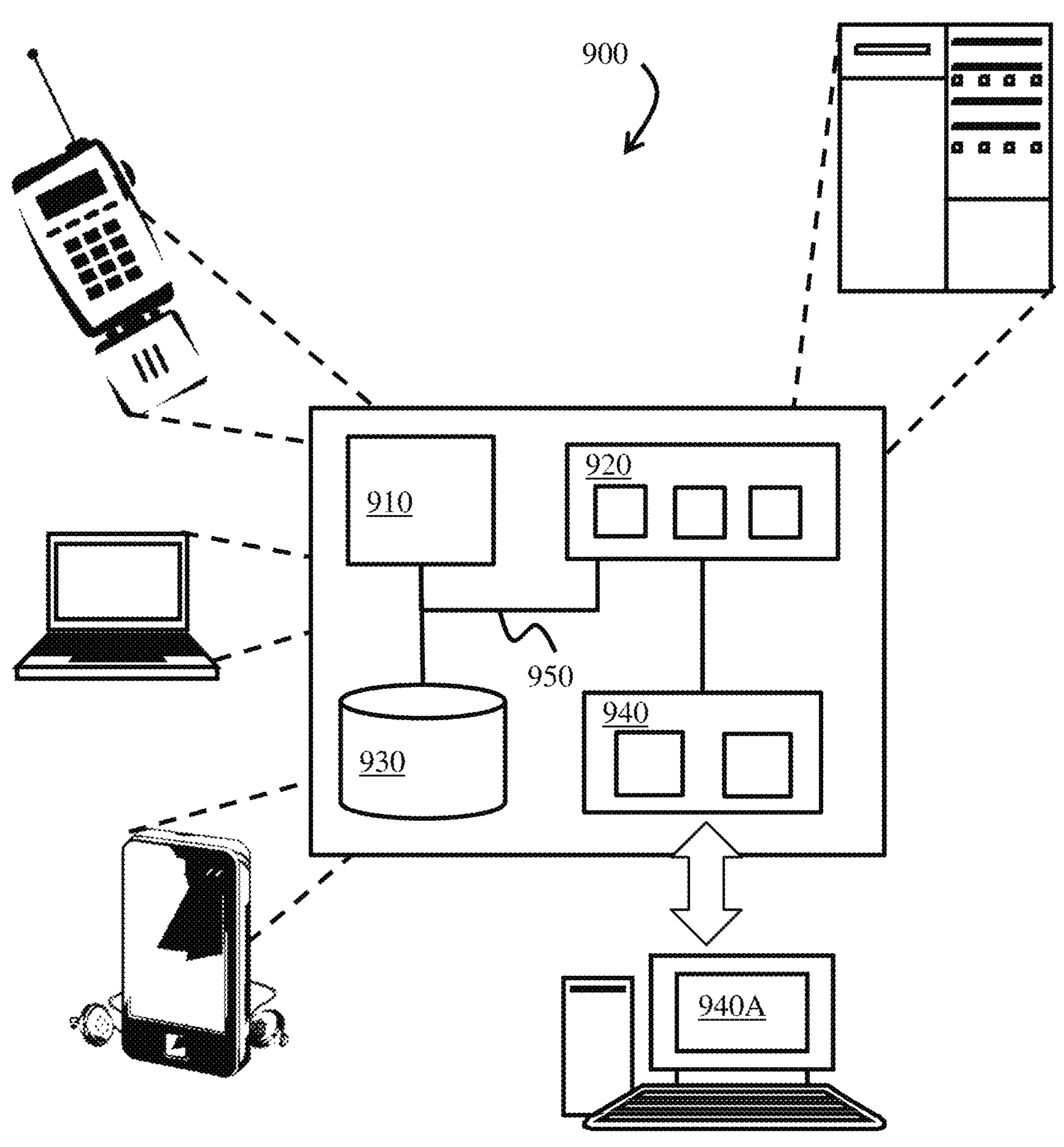
FIG. 9 illustrates one example embodiment of a computer system suitable for a state assessment system.

FIG. 9 is a schematic diagram of one embodiment of a computer system 900 by which the state assessment methods may be carried out. The computer system 900 can be used for the operations described in association with any of the computer implemented methods described herein. The computer system 900 includes at least one processor 910, a memory 920 and an input/output device 940. Each of the components 910, 920, and 940 are operably coupled or interconnected using a system bus 950. The computer system 900 may further comprise a storage device 930 operably coupled or interconnected with the system bus 950.

The processor 910 is capable of receiving the instructions and/or data and processing the instructions of a computer program for execution within the computer system 900. In some embodiments, the processor 910 is a single-threaded processor. In some embodiments, the processor 910 is a multi-threaded processor. The processor 910 is capable of processing instructions of a computer stored in the memory 920 or on the storage device 930 to communicate information to the input/output device 940. Suitable processors for the execution of the computer program instruction include, by way of example, both general and special purpose microprocessors, and a sole processor or one of multiple processors of any kind of computer.

The memory 920 stores information within the computer system 900. Memory 920 may comprise a magnetic disk such as an internal hard disk or removable disk; a magneto-optical disk; an optical disk; or a semiconductor memory device such as PROM, EPROM, EEPROM or a flash memory device. In some embodiments, the memory 920 comprises a transitory or non-transitory computer readable medium. In some embodiments, the memory 920 is a volatile memory unit. In another embodiments, the memory 920 is a non-volatile memory unit.

The processor 910 and the memory 920 can be supplemented by, or incorporated in, ASICs (application-specific integrated circuits).

The storage device 930 may be capable of providing mass storage for the system 900. In various embodiments, the storage device 930 may be, for example only and not for limitation, a computer readable medium such as a floppy disk, a hard disk, an optical disk, a tape device, CD-ROM and DVD-ROM disks, alone or with a device to read the computer readable medium, or any other means known to the skilled artisan for providing the computer program to the computer system for execution thereby. In some embodiments, the storage device 930 comprises a transitory or non-transitory computer readable medium.

In some embodiments, the memory 920 and/or the storage device 930 may be located on a remote system such as a server system, coupled to the processor 910 via a network interface, such as an Ethernet interface.

The input/output device 940 provides input/output operations for the system 900 and may be in communication with a user interface 940A as shown. In one embodiment, the input/output device 940 includes a keyboard and/or pointing device. In some embodiments, the input/output device 940 includes a display unit for displaying graphical user interfaces or the input/output device 940 may comprise a touchscreen. In some embodiments, the user interface 940A comprises devices such as, but not limited to a keyboard, pointing device, display device or a touchscreen that provides a user with the ability to communicate with the input/output device 940.

The computer system 900 can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, wireless phone networks and the computers and networks forming the Internet.

Although this invention has been described in the above forms with a certain degree of particularity, it is understood that the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention which is defined in the claims and their equivalents.

We claim:

1. A state assessment system configured to determine a state of a subject, the state assessment system comprising:

a physiological sensor comprising an fNIRS sensor configured to communicate a physiological data of a subject;

an additional sensor configured to communicate a cardiac data of the subject;

an analytics subsystem configured to determine a state of the subject from the physiological data and the cardiac data;

the fNIRS sensor comprises:

one or more LED, and one or more photodetector; and the analytics subsystem comprises:

a hemoglobin estimation module configured to determine a hemoglobin measure from the physiological data of the subject, a neurocognitive measure module configured to determine a neural activation measure from the hemoglobin measure, a heart rate measure module configured to determine a heart rate measure from the cardiac data of the subject, a physiology/state model configured to define a relationship between the neural activation measure and a cognitive state measure, and a cognitive state measure module configured to determine the state of the subject based on the cognitive state measure and the heart rate measure.

2. The state assessment system of claim 1 wherein the state of the subject comprises an objective measure of a workload measure.

3. The state assessment system of claim 1 wherein the state of the subject comprises an objective measure of one of the group of objective measures consisting of:

a vigilance measure;

a response inhibition measure; and a resilience measure.

4. The state assessment system of claim 2 wherein an attention measure and the workload measure are used to define a preparedness measure.

5. A method of training a physiology/state model for use to determine a state of a subject based on a physiological data of the subject, the method comprising:

defining a state of the subject as an attention measure and a workload measure;

defining the physiological data as a neural activation of the subject;

placing a sensor on the subject to measure the neural activation of the subject;

defining an objective relationship of the attention measure to the neural activation of the subject over a time period by performing a Continuous Performance Test (CPT) on the subject and measuring the neural activation of the subject over the time period; and defining an objective relationship of the workload measure to the neural activation of the subject over a second time period by performing an n-back task on the subject and measuring the neural activation of the subject over the second time period.

6. The method of claim 5 wherein the objective relationship of the attention measure to the neural activation of the subject over the time period and the objective relationship of the workload measure to the neural activation of the subject over a second time period are defined by a machine learning algorithm.

7. The method of claim 5 wherein the attention measure comprises a vigilance measure and a response inhibition measure.

8. The method of claim 5 wherein the n-back task comprises one or more NASA Task Load Index task.

9. The method of claim 5 further comprising;

placing a second sensor on the subject to measure the a heartrate measure of the subject; and the physiological data further comprises the heartrate measure of the subject.

10. The method of claim 5 further comprising:

placing a second sensor on the subject to measure a respiration measure; and the physiological data further comprises the respiration measure of the subject.

11. The method of claim 5 further comprising:

placing a second sensor on the subject to measure a hydration measure the subject; and wherein the physiological data further comprises the hydration measure of the subject.

12. The method of claim 5 further comprising:

placing a second sensor on the subject to measure a blood oxygen saturation measure of the subject; and wherein the physiological data further comprises the blood oxygen saturation measure of the subject.

13. The method of claim 5 wherein the physiological data further comprises at least one selected from the group of measures consisting of:

a heartrate measure of the subject;

a hydration measure the subject;

a hydration measure the subject; and a blood oxygen saturation measure of the subject.

14. A state assessment system configured to determine a state of a subject, the state assessment system comprising:

a physiological sensor comprising an fNIRS sensor configured to communicate a physiological data of a subject;

an additional sensor configured to communicate a cardiac data of the subject;

an analytics subsystem configured to determine a state of the subject from the physiological data and the cardiac data;

the fNIRS sensor comprises:

one or more LED, and one or more photodetector; and the analytics subsystem comprises:

a hemoglobin estimation module configured to determine a hemoglobin measure from the physiological data of the subject, a neurocognitive measure module configured to determine a neural activation measure from the hemoglobin measure, a heart rate measure module configured to determine a heart rate measure from the cardiac data of the subject, a physiology/state model configured to define a relationship between the neural activation measure and a cognitive state measure, a cognitive state measure module configured to determine the state of the subject based on the cognitive state measure and the heart rate measure, and the state of the subject comprises an objective measure of one of the group of objective measures consisting of:

a vigilance measure, a response inhibition measure, and a resilience measure.

* * * * *